United States Patent [19]

Vancaillie

[11] Patent Number: 5,095,917
[45] Date of Patent: Mar. 17, 1992

[54] TRANSUTERINE STERILIZATION APPARATUS AND METHOD

[76] Inventor: Thierry G. Vancaillie, 2703 Castanet, San Antonio, Tex. 78230

[21] Appl. No.: 447,882

[22] Filed: Jan. 19, 1990

[51] Int. Cl.$^5$ .............................. A61F 6/06
[52] U.S. Cl. .................... 128/831; 604/55; 606/28
[58] Field of Search ............. 604/11, 15, 49, 54–55; 606/40, 49, 50, 119, 135, 28; 128/788, 830–831, 833

[56] References Cited

U.S. PATENT DOCUMENTS

| | | |
|---|---|---|
| 3,840,016 | 10/1974 | Lindemann ..................... 606/49 |
| 4,057,063 | 11/1977 | Grieles et al. .................. 606/40 |
| 4,185,618 | 1/1980 | Corey ........................ 604/55 X |
| 4,416,660 | 11/1983 | Dafoe ........................... 604/55 |
| 4,606,336 | 8/1986 | Zeluff ........................ 604/55 X |
| 4,700,701 | 10/1987 | Montaldi ..................... 604/55 X |

Primary Examiner—C. Fred Rosenbaum
Assistant Examiner—Corrine Maglione
Attorney, Agent, or Firm—Pravel, Gambrell, Hewitt, Kimball & Krieger

[57] ABSTRACT

A method and apparatus for sterilization of females using a transuterine technique. The method of the present invention provides an irreversible method of sterilization which involves destruction of the mucosa followed by insertion of a biodegradable plug. The mucosal destruction provokes an inflammatory reaction and the plug serves as a substrate to guide the healing process toward occlusion instead of recanalization.

8 Claims, 6 Drawing Sheets

TRANSUTERINE STERILIZATION APPARATUS AND METHOD

FIELD OF THE INVENTION

The present invention relates generally to the field of human sterilization. More specifically, the present invention provides a method for providing an outpatient technique for sterilization of females using a transuterine technique.

BACKGROUND

With the 5 billion level in world population growth reached earlier than predicted by the convention of Rome, there is a desperate need for a reliable method of female sterilization. In addition, such a method must be inexpensive, easy to perform, and void of significant side effects or complications.

There is agreement that a transcervical approach is the least aggressive method and is considered "nonsurgical." In the prior art, three different methods have been investigated on a large scale. In one technique, investigators have inserted a unipolar electrical probe through the hysteroscope into the proximal isthmus of the tube. This technique has resulted in successful occlusion of the oviduct in up to 95% of cases, sometime requiring a second procedure. Significant complications have occurred with this technique, however, such as thermal injury to the bowel and ectopic pregnancy.

Another approach consists of transcervical instillations of quinacrine (Q). Major drawbacks of this method are the need for repeated applications and a significant level of side effects. Hysteroscopic filling of the tubes with silicone formed-in-place plugs has yielded approximately a 90% success rate for first attempts. This technique is time-consuming, however, and requires a high level of technical skill both for the preparation of the silicone and for performing the procedure.

SUMMARY OF THE INVENTION

The prior art methods discussed above consist of either destruction of the endosalpinx or obstruction of the lumen. The method of the present invention provides an irreversible method of sterilization, discussed in greater detail hereinbelow, which combines destruction of the mucosa with the insertion of a biodegradable plug. The mucosal destruction provokes an inflammatory reaction and the plug serves as a substrate to guide the healing process toward occlusion instead of recanalization. The fact that mucosal destruction is performed close to the uterus substantially lowers the risk of bowel injury. No caustic substance comes into contact with the peritoneum, obviating unpleasant side effects, and total occlusion of the lumen virtually eliminates the risk of ectopic pregnancy. Furthermore, no special technical skill is required to perform the procedure.

The method according to the present invention comprises the steps of destroying a superficial layer of the uterotubal junction and inserting means for promoting growth of scar tissue at said point of destruction of said uterotubal junction. The apparatus according to the present invention comprises means for destroying a superficial layer of the uterotubal junction; means for inserting means for promoting growth of scar tissue at the point of said destruction, thereby causing occlusion of said uterotubal junction. In the preferred embodiment of the present invention, the means for promoting growth comprises a biodegradable plug which may be formed from suture material or other suitable biodegradable material.

DETAILED DESCRIPTION OF THE PREFERRED EMBODIMENT

Figure 1:
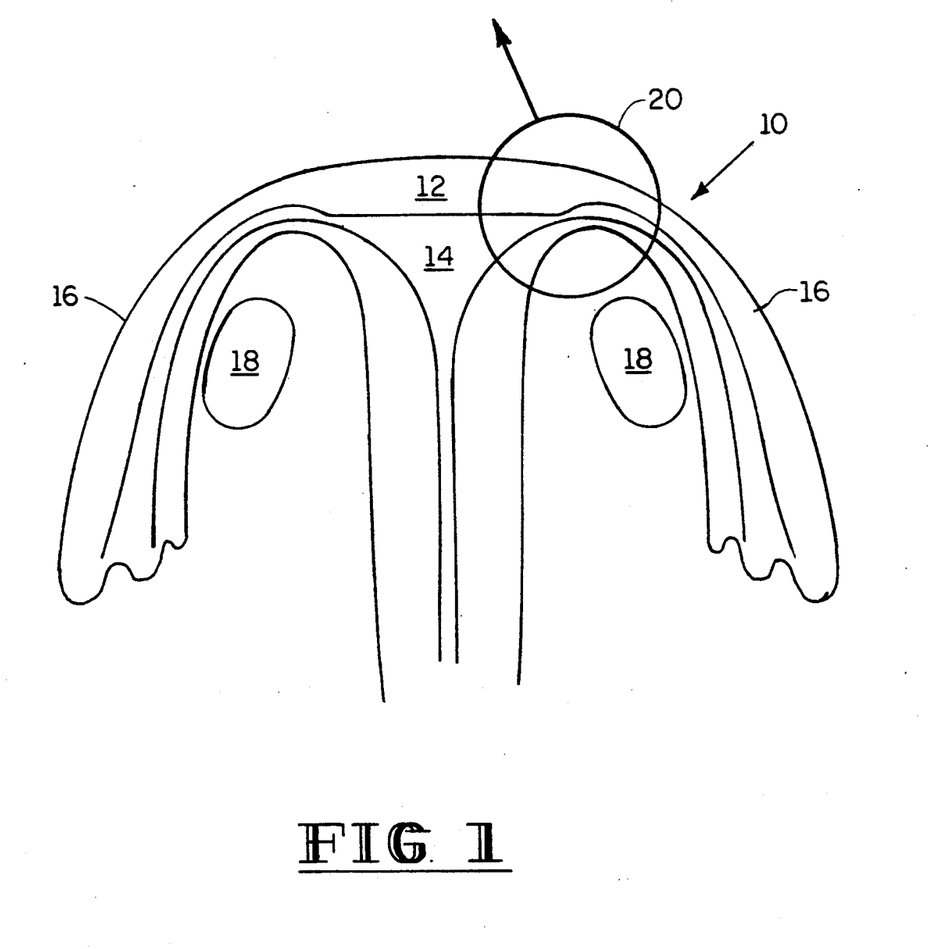
FIG. 1 is an illustration of the major components of the female reproductive system.
Figure 1A:
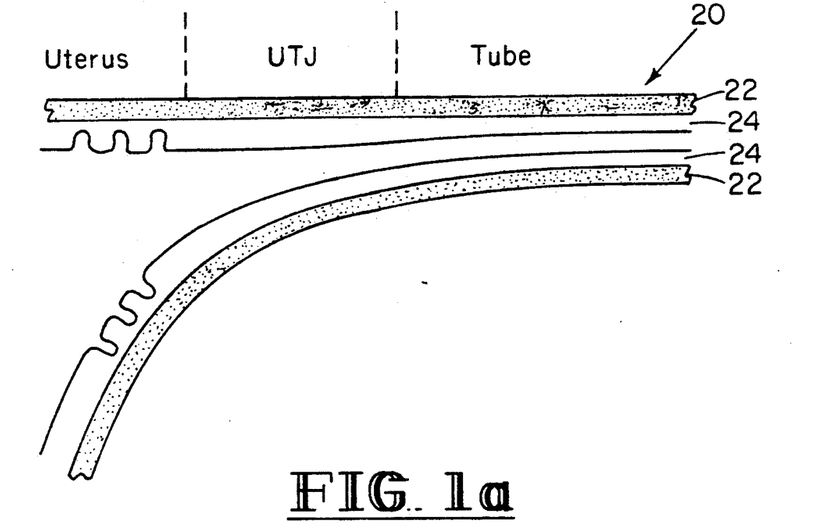
FIG. 1a is a graphical illustration of the uterotubal junction showing the tissue zone to be destroyed prior to the insertion of the biodegradable plug.

FIG. 1 shows some of the major elements of the female reproductive system 10. The uterus is an organ of the female pelvis that has the shape of a pear. It consists of a thick muscular coat, the "myometrium" 12, and a cavity having an inner mucosal lining of variable thickness, the endometrim 14. The tube 16 is a hollow organ that connects the uterus to the ovary 18. The ovary 18 is the organ that produces one or more egg every cycle of a woman's reproductive life. In the female reproductive system, there is one uterus, two tubes and two ovaries (under normal conditions). The site where tube and uterus connect is called the uterotubal junction illustrated by reference number 20 in FIG. 1. It is a section of tubular shape of about 10 mm. in length. Its diameter in the resting position is less than 1 millimeter, but when gas or liquid is pushed through the uterus and tubes, the diameter of the uterotubal junction is stretched up to 1.7 to 2 mm. FIG. 1a is an illustration of the uterotubal junction (UTJ) comprising layers of muscle 22 and mucosa 24.

The sterilization method of the present invention can be performed using any combination of tissue destruction and insertion of a biodegradable plug. Experiments have shown, however, that an instrument combining bipolar electrical current with a hollow tube containing the biodegradable plug (e.g. any suture material) is the most cost effective and practical set up.

Figure 2:
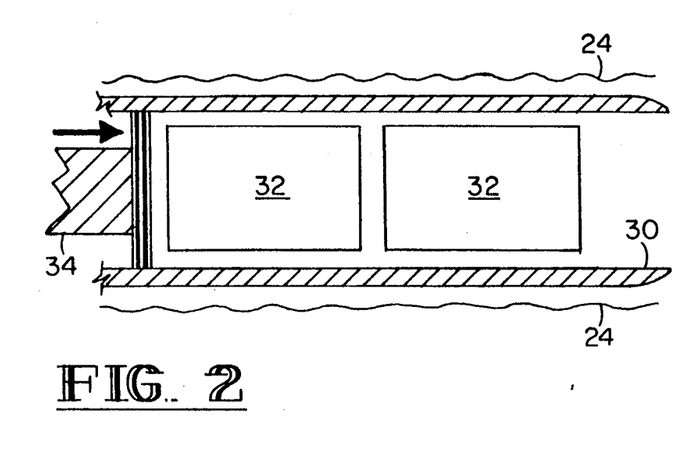
FIG. 2 is an illustration of the disposable instrument for combined bipolar current application and insertion of the biodegradable plug.
Figure 2A:
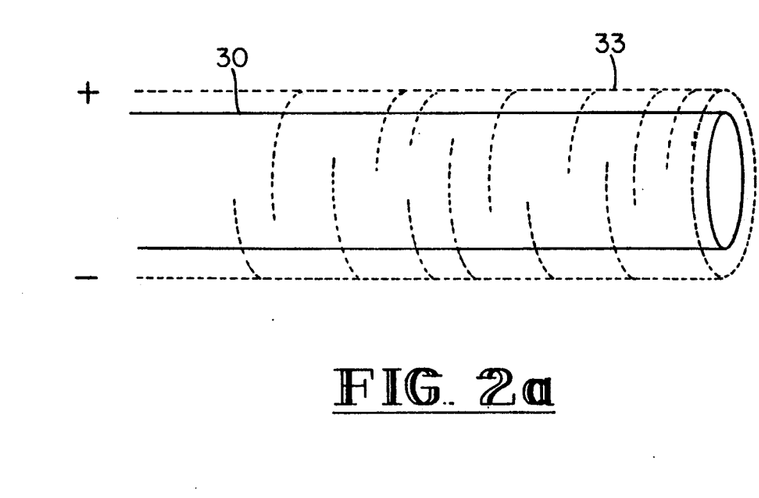
FIG. 2a is an illustration of wiring on the outer surface of the insertion instrument of the present invention.

The sterilization instrument used in the present invention comprises a hollow tube 30 with an outer diameter of approximately 2 mm and an inner diameter of approximately 1 to 1.5 mm (length approximately 35 cm) containing two or three plugs 32 having dimensions of approximately 1.0 mm × 10 mm. The plugs 32 are comprised of any biodegradable material. They may or may not contain a drug such as tetracycline hydrochloride, which delays breakdown of the initial clot and therefore, enhances scarification. The plugs 32 can be moved forward, i.e. out of the hollow tube 30, by pushing a piston 34 (similar to a syringe). The tube 30 could contain more than two plugs 32, for in some cases a plug could prematurely be pushed out of the tube 30. The hollow tube 30 is fitted with copper wiring 33 on the outside, for connection to a high frequency bipolar current generator via electrical cables 37, shown in FIG. 2.

Figure 3:
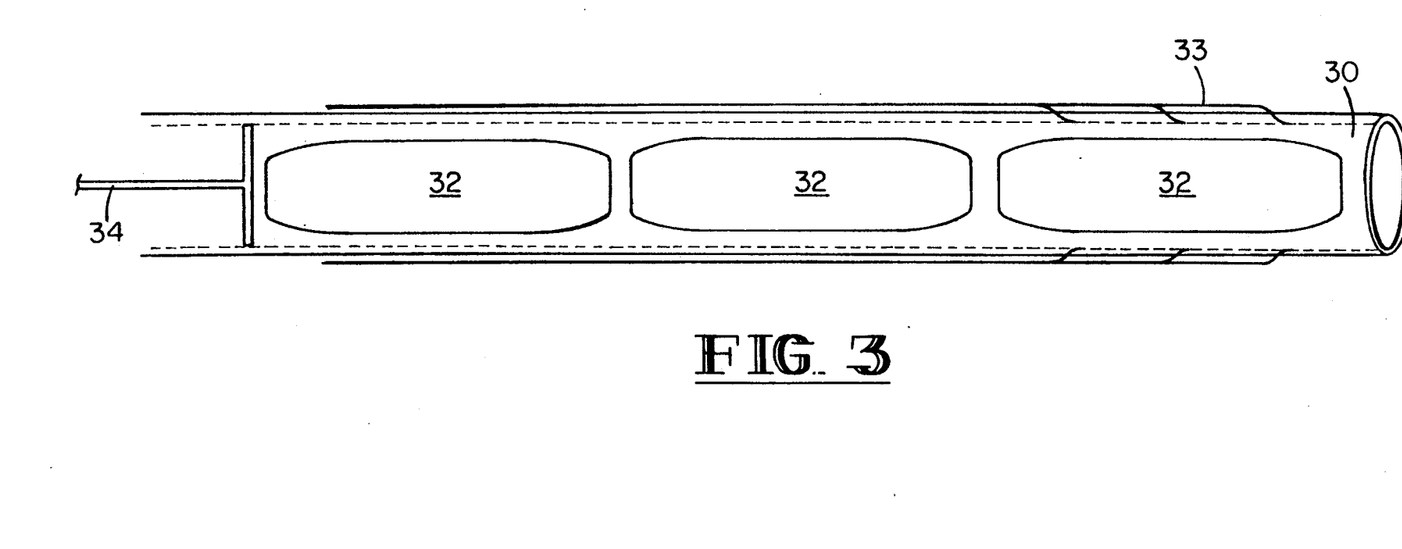
FIG. 3 is a diagram of the sterilization instrument showing multiple plugs contained therein.
Figure 4:
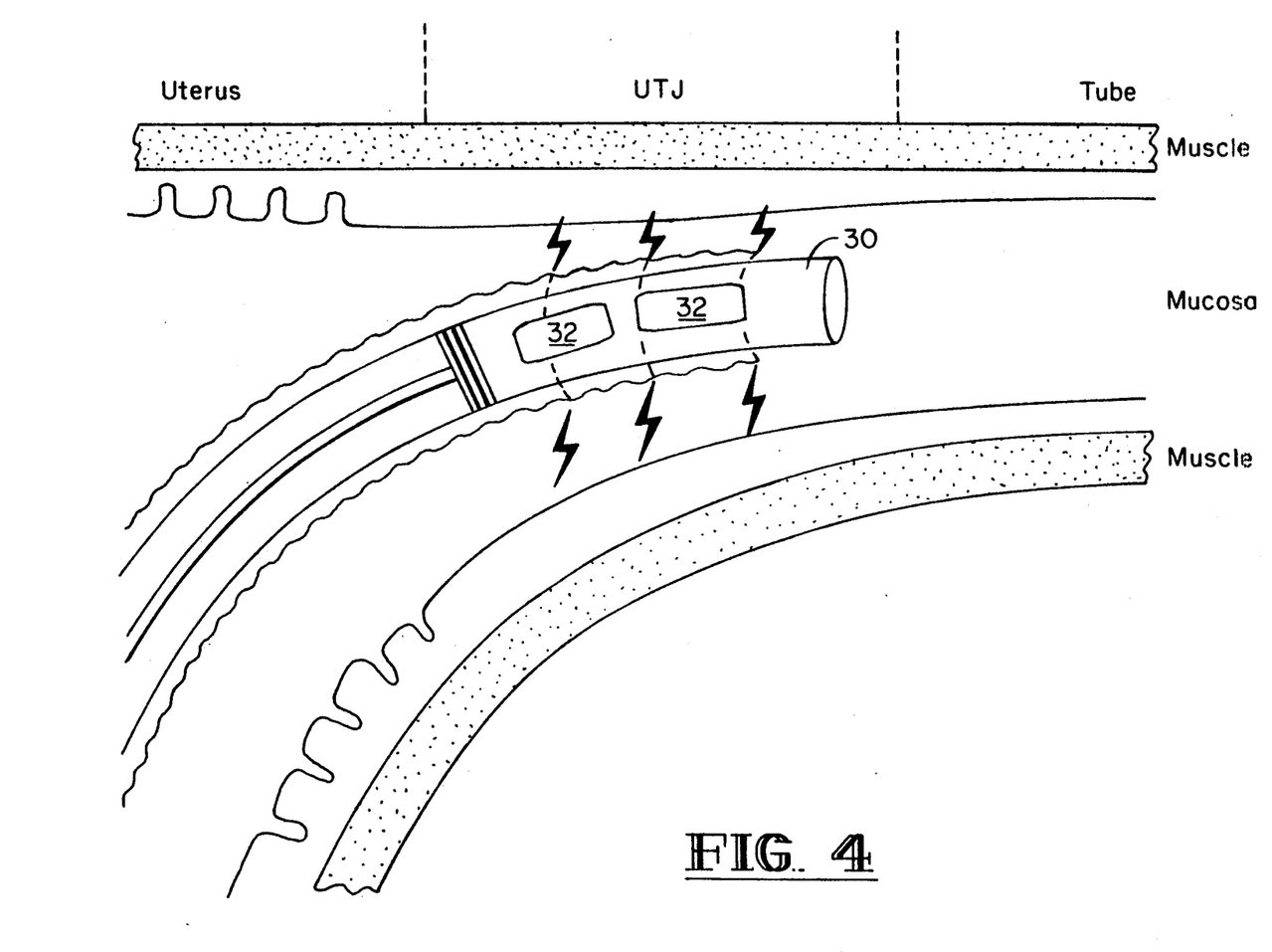
FIG. 4 is an illustration of the instrument inserted into the uterotubal junction.
Figure 5:
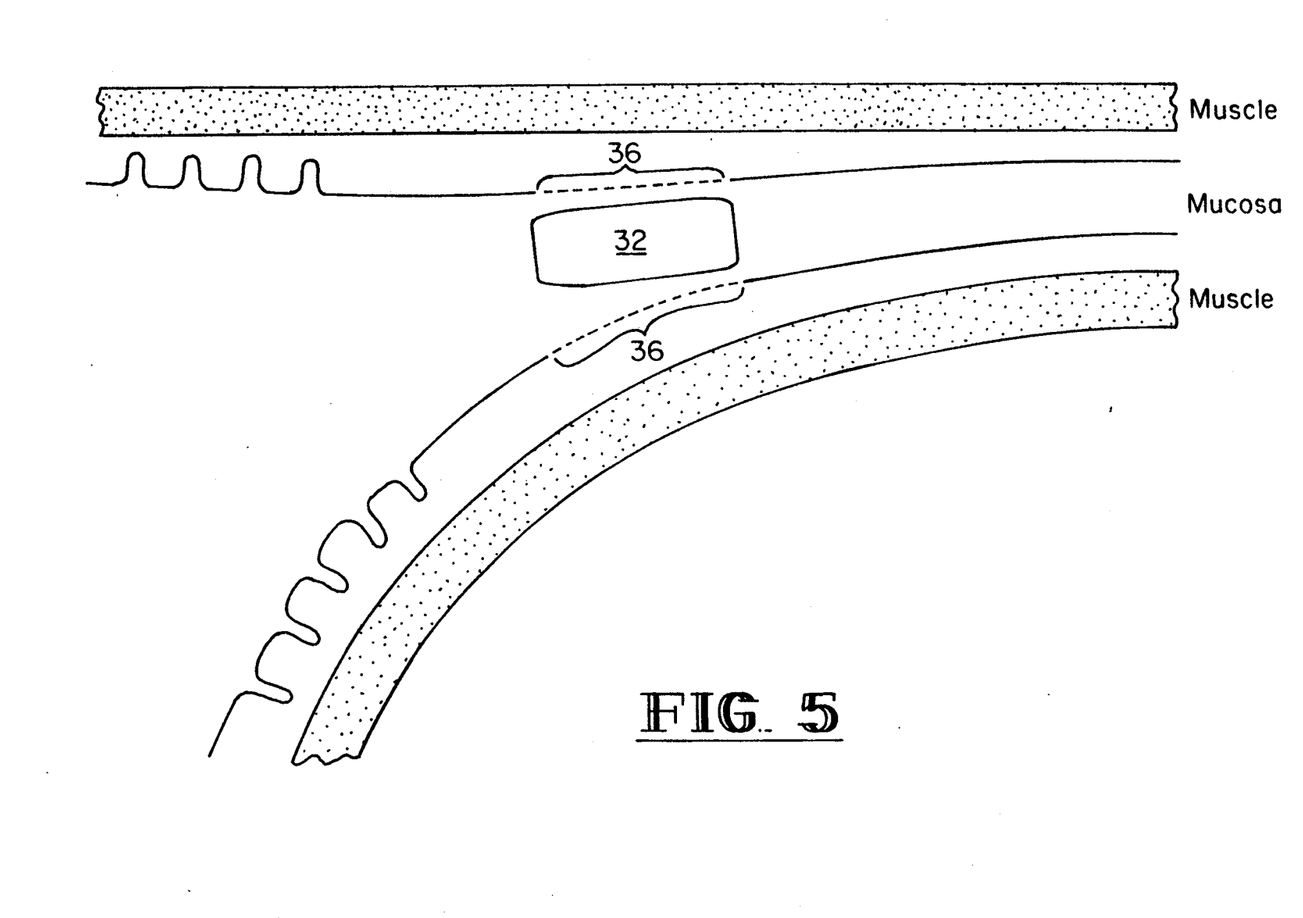
FIG. 5 is an illustration of the uterotubal junction after insertion of the biodegradable plug.

FIG. 3 is an elevational side view of the above-described instrument containing three plugs 32 of biodegradable material. FIG. 4 is an illustration of the instrument inserted into the reproductive system, with the current activated to cause destruction of a portion of the mucosa within the UTJ. In operation, bipolar coagulation current of approximately 5 watts for a duration between 5 and 15 seconds is sufficient to produce irreversible but shallow thermal damage of the tubal mucosa. After bipolar coagulation of the uterotubal junction, the piston 34 of the instrument is activated and the instrument simultaneously slightly withdrawn. This will result in the release of one plug 32 that will then be at the exact level of the destroyed mucosa of the uterotubal junction. The same is repeated in the UTJ on the other side of the reproductive system. FIG. 5 shows a plug 32 inserted within the UTJ in the zone of destruction of mucosa, illustrated by reference numeral 36.

Figure 6:
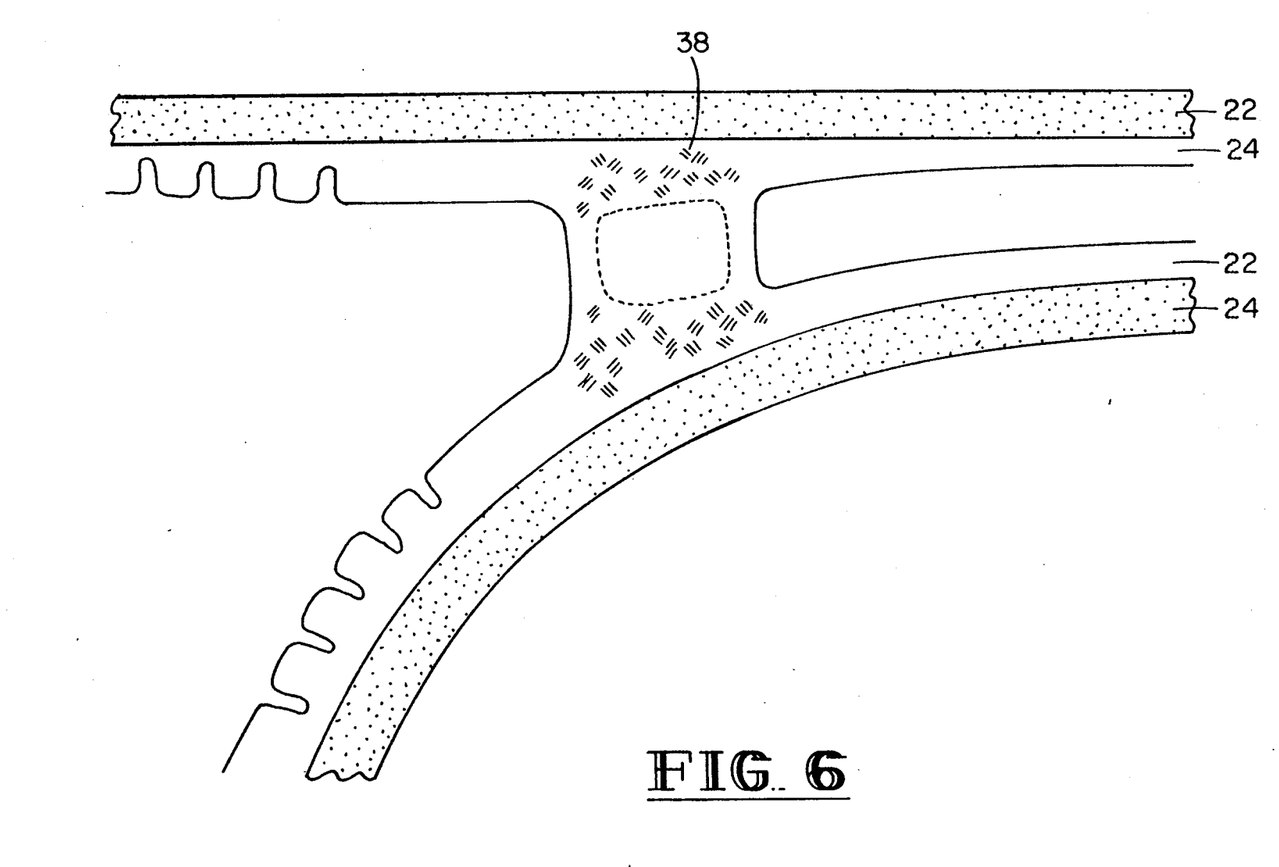
FIG. 6 is the expected postoperative result resulting in sterilization of the reproductive system.

The application of bipolar electrical energy causes an immediate inflammatory reaction. Part of this reaction is "edema" i.e. tissue swelling. This natural mechanism will keep the plug in its position. Inflammatory cells (polymorphonuclear cells—white blood cells) leave the vessels and colonize the injured tissue. They initally work at "sealing the area off." Then they and other cells work at repairing the injury. Part of this process is that fibroblasts (i.e. cells that form the connective tissue) proliferate. This process of proliferation can be enhanced by some drugs such as tetracycline hydrochloride, contained in the plug. Due to the presence of the plug, fibroblasts will not only colonize the injured tissue, but also the plug. Other cells such as the macrophages will "clean up" the area, which will also assist in digesting the material the plug is made of. After a period of 3-6 weeks, cells gradually disappear and leave behind them a dense structure of fibers known as scar tissue, illustrated by reference numeral 38 in FIG. 6, which will also include the area in which the plug was inserted. This process therefore results in irreversible occlusion of the tubal lumen, as illustrated in FIG. 6, thereby rendering the patient sterile.

The electrical current serves as the method for destruction of the endosalpinx. A plug 32 acts as a matrix for ingrowth of fibroblasts and as a substrate for reepithelialization with endometrial mucosa. The plug 32 used in the preferred embodiment is a polymer with both hydrophilic and hydrophobic properties. This particularity gives the polymer a tremendous capacity of expansion, which can be precisely defined through variation of the proportions of the different compounds of the polymer. Other materials such as e.g. common suture material could be used.

The reasons for selection of this material are as follows: (1) expansion of the plug by uptake of water ensures that the plug fits into the uterotubal junction independent of the diameter of the latter, and (2) a drug that stimulates proliferation of fibroblasts could be incorporated into the plug to enhance the process of tubal occlusion. The plug used in the method of the present invention has a rod-like shape, 10 mm long and 1 mm in diameter.

The endosalpinx has the ability to defend itself against chemical or infectious agents and is even capable of regeneration. This property of the endosalpinx has been the major problem in previous attempts at intrauterine sterilization, using chemicals like quinacrine or tetracycline. However, this process of regeneration seems to be time-consuming as shown by the delay in the occurrence of an occasional intrauterine pregnancy after successful tubal ligation.

The endometrium has a tremendous potential to regenerate, as illustrated by the menstrual cycle in se. Even after partial destruction of the stratum basalis, regrowth of the endometrium occurs very rapidly.

The difference in the kinetics of regeneration is the basis for the assumption that when the transition zone between endosalpinx and endometrium is destroyed, the endometrium tends to invade the fallopian tubes. Following destruction of the transition between the two mucosas, regenerating endometrium will presumably replace the destroyed endosalpinx.

By manipulating the strong tendency of the endometrium to regenerate, occlusion of the ostium tubae may be obtained, with resultant irreversible sterilization. Endometrium has been shown to regenerate rapidly, even if the continuity of the stratum basalis is interrupted. Reepithelialization of the uterine wall has been found to be possible in less than one menstrual cycle, following resection of a uterine septum. Furthermore it has been determined that the remnants of endometrial tissue have the ability to epithelialize the entire uterine cavity following surgical removal of the adhesions of Asherman's syndrome. It should be noted however, that following such surgery, it is necessary to distend the uterine cavity mechanically with an IUD to avoid contact between the anterior and posterior walls during the process of reepithelialization, thus preventing the formation of synechiae.

The difference in regenerative ability between the endometrium and the endosalpinx is illustrated by the healing process following an acute infection. Experiments have shown that three months after a proved acute pelvic inflammatory disease, the endosalpinx was still congested, whereas the endometrium presented a completely normal appearance. Peculiar to the ostium tubae was the appearance of neovascularization arising on the surface of the endometrium and growing into the endosalpinx. This demonstrates that an inflammatory insult at the level of the ostium tubae releases an endometrial mechanism of regeneration similar to that which happens, for example, following the resection of a septum, and illustrates the tendency to invade the endosalpinx.

EXPERIMENTAL RESULTS

Fourteen New Zealand White-Cambridge does were anesthetized with zylazine hydrochloride (19 mg/kg intramuscularly), and ketamine hydrochloride (50 mg/kg intramuscularly). A median laparotomy was performed to expose the two uterine horns. A transverse uterotomy on both sides, halfway between the uterotubal junction and vagina, gave access to the uterine cavities. A hysteroscope was inserted successively into the right and the left uterine cavities, with glucose 5% used as the distention medium. A bipolar probe 2 mm in diameter with an uninsulated tip 1.5 mm long, especially designed for this experiment, was inserted through the operating channel of the endoscope. In the rabbit, abundant mucosal folds mask viewing of the tubal ostium. To ensure proper placement of the probe at the level of the uterotubal junction, the probe was inserted 1.5 cm into the tubal lumen, which could be visually assessed from the outside. Then the probe was slowly withdrawn until the edge of the insulated sheath was visible. This procedure ensured proper contact between the uninsulated tip of the probe and the uterotubal junction. An electrical current was applied for 5 seconds with a power output of 4.8 W. This caused blanching of the tissue over a circular area approximately 2 mm wide. The bipolar probe was exchanged for a cannula containing the plug, which was inserted into the uterotubal junction. The plug is made of a substance called Aqualloy (Aqualloy, Drachten, The Netherlands), and extracted into 10×1 rods by the Southern Research Institute (Birmingham, AL).

The rabbits were divided into two groups of seven. In group A, the plug inserted on the right side contained 4 mg. of Q. In group B, the plug on the right side contained 20 $\mu$l of platelet extract (PE) from 20 ml rabbit blood. The plugs inserted on the left side (n=14) of both groups were untreated.

The uterotomy and abdomen were closed layer by layer. The animals were observed until total recovery and housed in individual cages under standard conditions. Postoperatively, endometrial growth was stimulated by intramuscular administration of 30 ug/kg estradiol cypionate every 4 days starting on day 0 to simulate the proliferative phase in humans. One animal of each group was killed on days 3, 6, 9, 12, 15, 18, and 21. Serial longitudinal sections (30 or more) were obtained and stained with hematoxylin and eosin. The following morphologic features were considered to indicate tubal occlusion: (1) interruption of the continuity between the mucosal lining of the endometrium and the endosalpinx, (2) contact of the plug with the area of mucosal interruption, (3) observation of fibroblasts directly on the surface of the plug at the site of mucosal interruption, and (4) filling of grooves and surface defects of the plug with connective tissue.

All but one procedure led to total occlusion of the tubal lumen. Occlusion of the tubal lumen was histologically assessed by the presence of the above mentioned criteria. Dense connective tissue surrounding the plug could be demonstrated as early as postoperative day 3 in all groups. The ratio of connective tissue to fibroblasts gradually increased with the length of the postoperative period. When cutting artifacts occurred because of the difference in consistency between the tissue and the plug, direct contact between the plug and the connective tissue was assessed by the fact that fibroblasts remained attached to the surface of the plug at the level of the artifact. Polymorphonuclear cells were present in small numbers at days 3 and 6, and disappeared by day 9. Leukocytes and some rare plasmocytes were present at all times. There was no giant cell infiltration or any indication of host-graft reaction. By day 18, vessels appeared growing into the scar tissue surrounding the plug. No measurable difference in inflammation was seen between the controls and the treatment groups or among treatment groups. In the one specimen of Group A considered a failure, the plug could not be located, and the uterotubal junction had a normal appearance with continuity of the mucosal lining. This specimen was sampled on day 12 and no histologic evidence of previous thermal injury could be detected. This failure in an animal of the control group is not attributed to the absence of the drug, but rather to dislocation of the plug, probably immediately or very soon after insertion. Indeed, the procedure had been technically difficult because of a sharp angle between uterus and tube at the level of the uterotubal junction and because of the small diameter of the tubal lumen in the particular animal.

This study demonstrates that a combination of minimal mucosal damage and insertion of a plug leads to occlusion of the tubal lumen, as assessed by histologic criteria. Of interest is that fibroblasts cast the Aqualloy plug at the site of mucosal destruction as early as postoperative day 3. The natural inflammatory process seems to be adequate, and was not enhanced by the added drugs. However, other drugs, such as tetracycline, will be examined and might well increase the postoperative scarring around the plug.

The fact that histologic examination of the specimen with lost plug revealed a well-healed mucosa 12 days after the procedure indicates that the thermal damage inflicted by the bipolar current is minimal. Compared with previous methods using electrical current for coagulation of the endosalpinx, this technique is definitely safer, because the bipolar mode is used at a very low power output and because the current is applied at the level of the uterotubal junction rather than the proximal isthmus, therefore virtually eliminating the risk of perforation and thermal damage to the bowel. Although the method and apparatus of the present invention has been described in connection with the preferred embodiment, it is not intended to be limited to the specific form set forth herein, but, on the contrary, it is intended to cover such alternatives, modifications and equivalents as can reasonably be included within the spirit and scope of the invention as defined by the appended claims.

What is claimed is:

1. An apparatus for causing sterilization of a female reproductive system, comprising:
    vaginally insertable means for destroying a superficial layer of the uterotubal junction at a selected location; and
    means for inserting a biodegradable plug at said point of destruction of said superficial layer of said uterotubal junction, said biodegradable plug being impregnated with means for promoting scar formation, said means for promoting said scar formation comprising tetracycline hydrochloride, said means for inserting being carried with said means for destroying said superficial layer of the uterotubal junction.

2. The apparatus according to claim 1, said means for destroying said superficial layer of said uterotubal junction comprising a generally tubular apparatus having electrical conduction means on the outside thereof for connection to a high frequency generator.

3. The apparatus according to claim 2, said means for providing electrical current comprising means for providing a bipolar coagulating current.

4. The system according to claim 3, said tubular apparatus containing multiple biodegradable plugs and means for urging said plugs from said container for implantation into said uterotubal junction.

5. A method for sterilization of a female reproductive system, comprising the steps of:
    destroying a superficial layer of the uterotubal junction; and
    inserting a biodegradable plug at said point of destruction of said superficial layer of said uterotubal junction, said biodegradable plug being impregnated with means for promoting scar formation, said means for promoting said scar formation comprising tetracycline hydrochloride.

6. The method according to claim 5, said means for destroying said superficial layer of said uterotubal junction comprising a generally tubular apparatus having electrical conduction means on the outside thereof for connection to a high frequency generator.

7. The method according to claim 6, said means for providing electrical current comprising means for providing a bipolar coagulating current.

8. The method according to claim 7, said tubular apparatus containing multiple biodegradable plugs and means for urging said plugs from said container for implantation into said uterotubal junction.

* * * * *

UNITED STATES PATENT AND TRADEMARK OFFICE
CERTIFICATE OF CORRECTION

PATENT NO. : 5,095,917

DATED : 03/17/92

INVENTOR(S) : THIERRY G. VANCAILLIE

It is certified that error appears in the above-identified patent and that said Letters Patent is hereby corrected as shown below:

On the title page, item [21] Appl. No.:
The correct serial number for Patent No. 5,095,917 is
467,882.

Signed and Sealed this

Twentieth Day of July, 1993

*Attest:*

MICHAEL K. KIRK

*Attesting Officer*   Acting Commissioner of Patents and Trademarks